(12) United States Patent
Martin

(10) Patent No.: US 9,448,159 B2
(45) Date of Patent: Sep. 20, 2016

(54) EPOXY MOLDED GAS CELL FOR OPTICAL MEASUREMENT AND METHOD OF FORMING

(71) Applicant: SENSEAIR AB, Delsbo (SE)

(72) Inventor: Hans Göran Evald Martin, Delsbo (SE)

(73) Assignee: Senseair AB (SE)

( * ) Notice: Subject to any disclaimer, the term of this patent is extended or adjusted under 35 U.S.C. 154(b) by 0 days.

(21) Appl. No.: 14/362,384

(22) PCT Filed: Nov. 30, 2012

(86) PCT No.: PCT/SE2012/000197
§ 371 (c)(1),
(2) Date: Jun. 2, 2014

(87) PCT Pub. No.: WO2013/081519
PCT Pub. Date: Jun. 6, 2013

(65) Prior Publication Data
US 2014/0333924 A1 Nov. 13, 2014

(30) Foreign Application Priority Data
Dec. 2, 2011 (SE) ........................................ 1151147

(51) Int. Cl.
| | |
|---|---|
| G01N 1/10 | (2006.01) |
| B29D 11/00 | (2006.01) |
| G01N 21/01 | (2006.01) |
| G01N 21/05 | (2006.01) |
| G01N 21/03 | (2006.01) |
| B29C 45/02 | (2006.01) |
| G01N 21/3504 | (2014.01) |

(Continued)

(52) U.S. Cl.
CPC ............... *G01N 21/01* (2013.01); *B29C 45/02* (2013.01); *G01N 21/031* (2013.01); *G01N 21/05* (2013.01); *B29K 2063/00* (2013.01); *B29K 2509/00* (2013.01); *B29L 2011/00* (2013.01); *B29L 2011/0083* (2013.01); *G01N 21/3504* (2013.01); *G01N 2021/0314* (2013.01); *G01N 2021/0378* (2013.01); *G01N 2201/0228* (2013.01)

(58) Field of Classification Search
CPC .... G01N 21/05; G01N 21/031; G01N 21/01; G01N 21/3504; G01N 2201/0228; G01N 2021/0314; G01N 2021/0378; B29C 45/02; B29K 2063/00; B29K 2509/00; B29L 2011/00; B29L 2011/0083
USPC ............................................. 356/246; 264/1.1
See application file for complete search history.

(56) References Cited

U.S. PATENT DOCUMENTS 3,613,026 A * 10/1971 Skolnick et al. ................ 372/32
3,773,424 A * 11/1973 Selgin ........................... 356/410

(Continued)

FOREIGN PATENT DOCUMENTS

| DE | 10321649 A1 | 12/2004 |
|---|---|---|
| DE | 1020047058815 A1 | 6/2006 |
| GB | 869047 * | 6/1959 |

*Primary Examiner* — Tarifur Chowdhury
*Assistant Examiner* — Sunghee Y Gray
(74) *Attorney, Agent, or Firm* — Foley & Lardner LLP (57) ABSTRACT

The present invention relates to a gas cell (1) for optical measurements of gas content and/or concentration comprising a cavity (1a), at least one aperture (11) for gas exchange, at least one first socket (12) for light emitting means (2) and at least one second socket (13) for light detecting means (3). The length of an optical measuring path (A) through the cavity (1a) is defined by a direct or indirect distance between a light emitting means (2) in the first socket (12) and a light detecting means (3) in the second socket (13). The present invention teaches that an epoxy mold compound is used to form at least the parts of the gas cell (1) that define the optical measuring path (A).

20 Claims, 4 Drawing Sheets (51) Int. Cl.
    *B29K 63/00*    (2006.01)
    *B29K 509/00*   (2006.01)
    *B29L 11/00*    (2006.01)

(56) References Cited

U.S. PATENT DOCUMENTS

| | | | | |
|---|---|---|---|---|
| 4,124,301 A * | 11/1978 | Pocock | | 356/432 |
| 8,852,513 B1 * | 10/2014 | Speer et al. | | 422/83 |
| 2002/0148289 A1 * | 10/2002 | Isogai et al. | | 73/204.26 |
| 2002/0191380 A1 * | 12/2002 | Val | | 361/760 |
| 2004/0052994 A1 * | 3/2004 | Geibel | | 428/35.7 |
| 2006/0181772 A1 * | 8/2006 | Byers et al. | | 359/512 |
| 2007/0133001 A1 * | 6/2007 | Cox et al. | | 356/437 |
| 2007/0151942 A1 | 7/2007 | Dishongh et al. | | |
| 2008/0179503 A1 | 7/2008 | Camargo et al. | | |
| 2009/0059235 A1 * | 3/2009 | Qu et al. | | 356/437 |
| 2009/0161108 A1 | 6/2009 | Frese et al. | | |
| 2010/0050879 A1 * | 3/2010 | Knox | | 96/413 |
| 2011/0090505 A1 | 4/2011 | Kuze et al. | | |
| 2012/0176616 A1 * | 7/2012 | Hunt et al. | | 356/338 |

* cited by examiner

EPOXY MOLDED GAS CELL FOR OPTICAL MEASUREMENT AND METHOD OF FORMING

FIELD OF INVENTION

The present invention relates to a gas cell for optical measurements of gas content and/or concentration in a macroscopic system where the length of the optical measuring path is in the range of centimeters. The gas cell comprises a cavity, at least one aperture for gas exchange, at least one first socket for incoming light and at least one second socket for light detecting means. The length of an optical measuring path through the cavity is defined by a direct or indirect distance between a light emitting means in the first socket and a light detecting means in the second socket. The present invention also relates to a method to form an inventive gas cell.

DESCRIPTION OF BACKGROUND ART

In the making of gas cells for optical measurements with optical measuring paths in the range of centimeters and longer, mechanical stability directly affects the stability of the sensor output and thus limits the accuracy of the sensor. Low cost gas cells are normally made through injection moulding with thermoplastic materials. Such gas cells normally deforms with changes in temperature and humidity, or when mechanical stress or forces reach the plastic. It is known to use high-performance thermoplastic materials that are possible to injection mould, such as liquid crystal polymer (LCP). It is also known to use metal if even better accuracy or stability is required. For instance highly sensitive leak detectors use metal optics and or metal mechanics, of course at a significantly higher production cost.

SUMMARY OF THE PRESENT INVENTION

Problems

In the making of gas cells for optical measurements with optical measuring paths in the range of centimeters and longer it is a problem to form cells with high mechanical stability and with a well defined and stable optical path-length between emitter and detector.

It is a problem to produce a reflecting surface that is sufficiently smooth to not distort the wave front of the emitted light as it is reflected, specifically when one measuring path may lead to several reflections in one or several reflecting surfaces, and at the same time stable and endurable regarding temperature variations and/or mechanical stress without introducing distortions in the wave front of the reflected light.

It is a problem to produce gas cells that can function in environments where there are environmental problems for components in the gas cell and where a good environmental protection can be provided to these components.

It is a problem to encapsulate components, such as detectors and emitters, without risking that wire-bond connections are getting broken and destroyed, and without covering parts of the components that are to be uncovered.

It is also a problem to integrate optical mirror functionality and heaters or other electronics inside the mirrors when using known technologies for making gas cells.

It is also a problem to take care of the condensation that appears on optical parts, specifically on reflecting surfaces, caused by temperature variations when the temperature is close to the dew point.

Solution

With the purpose of solving one or more of the above mentioned problems, and from the standpoint of the field of invention as defined above, a gas cell is proposed where an epoxy mold compound (EMC) has been used to form at least the part of the gas cell that defines the optical measuring path.

In the description of the present invention the term Ceramic Reinforced Encapsulation (CRE) will be used. For CRE a standard highly mineral filled Epoxy can be used, which is a blend that is very widely used mainly in the electronics IC packaging industry. The reason for the success of this material in the electronics components industry is that the material viscosity during the moulding process is so very low that even the tiniest electronic chips and their micro-meter thin wire-bond connections get embedded and fully filled by this moulding compound, without getting broken or destroyed.

The stability and the resolution of a gas sensor using a gas cell is highly dependent on the mechanical stability of the optical measuring path, meaning that the physical length of the measuring path needs to be well defined, stable and able to withstand mechanical stress and temperature variations which is specifically hard to achieve in a macroscopic system where the length of the optical measuring path is in the range of centimeters and longer, and meaning that the wave front of the emitted light remains without distortion when reflected of reflecting means in the gas cell, where these reflecting means are able to withstand mechanical stress and temperature variations which again is hard to achieve in macroscopic systems where the reflecting surfaces can be several square centimeters. The present invention teaches that an epoxy mold compound (EMC) is used to form the part of the gas cell that defines the optical measuring path, thus providing a measuring path that fulfills these requirements, however, it should be understood that it is possible to use an epoxy mold compound (EMC) to form more than the parts defining the optical measuring path, or even the complete gas cell.

The first socket is adapted to hold a light emitting means in its correct position. This can socket can be adapted to different ways of securing the light emitting means, such as through threaded screws, bayonet fastening, snap on fastening or by means of an adhesive, such as epoxy glue.

It is proposed that light emitting means is positioned in the first socket, and that the light emitting means is at least partly encapsulated in the EMC. Such encapsulation makes it possible to secure the light emitting means in its correct position without any other means of securing the light emitting means.

It is also possible that the light emitting means is covered by optically transparent material for protection, such as optically transparent EMC.

As described above for the securing of light emitting means in the first socket, the second socket can be adapted to secure the light detecting means in different ways. It is proposed that light detecting means is positioned in the second socket, and that the light detecting means is at least partly encapsulated in the EMC. Such encapsulation makes it possible to secure the light detecting means in its correct position without any other means of securing the light detecting means.

It is also possible that the light detecting means is covered by optically transparent material for protection. This could be optically transparent EMC or an optical filter which can provide not only protection but also means for separating wavelengths in the incoming light to be detected by the light detecting means from wavelengths that are not to be detected.

It is also proposed that the cavity comprises at least one light reflecting means, where the measuring path can includes a reflection in the light reflecting means. The light reflecting means can be a light reflecting mirror, which light reflecting mirror can be at least partly encapsulated in the EMC.

It is possible to position a piezo transducer behind the reflecting mirror, adapted to adjust the position of the reflecting mirror, which piezo transducer can be encapsulated in the EMC.

It is also possible that the light reflecting means is a reflecting surface, where the shape of the reflecting surface is formed in the EMC. This reflecting surface is then a part that defines the measuring path and it must in no way distort the wave front of the light in the measuring path.

It is proposed that heating means can be positioned behind the light reflecting means, which heating means can be encapsulated in the EMC.

Electronic components, such as amplifying means, computing means, memory means, or driver electronics for the light emitting means, related to the gas cell, can also be encapsulated in the EMC.

It is also possible to have optical components, such as optical filtering means, beam splitting means or optical gratings, related to the gas cell, at least partly encapsulated in the EMC.

It is also proposed that gas filtering means, such as filter to prevent contamination of the cavity, can be positioned in the aperture, where the gas filtering means is at least partly encapsulated in the EMC.

The present invention also relates to a method to form a gas cell for optical measurements of gas content and/or concentration comprising a cavity, at least one aperture for gas exchange, at least one first socket for a light emitting means and at least one second socket for a light detecting means, and where the length of an optical measuring path through the cavity is defined by a direct or indirect distance between a light emitting means in the first socket and a light detecting means in the second socket. The present invention specifically teaches that an epoxy mold compound (EMC) is used to form at least the part of the gas cell that defines the optical measuring path.

It is proposed that light emitting means are positioned in the first socket, which light emitting means is at least partly encapsulated in the EMC. These light emitting means can be covered by optically transparent material for protection, such as optically transparent EMC.

It is also proposed that light detecting means are positioned in the second socket, which light detecting means is at least partly encapsulated in the EMC. These light detecting means can be covered by optically transparent material for protection, such as optically transparent EMC or an optical filter.

The cavity can comprise at least one light reflecting means, where the measuring path includes a reflection in the light reflecting means.

The light reflecting means can be a light reflecting mirror, which light reflecting mirror can be at least partly encapsulated in the EMC.

A piezo transducer can be positioned behind the reflecting mirror, adapted to adjust the position of the reflecting mirror, and this piezo transducer can be encapsulated in the EMC.

The light reflecting means can also be a reflecting surface, where the shape of the reflecting surface can be formed in the EMC.

It is proposed that heating means can be positioned behind the light reflecting means, which heating means can be encapsulated in the EMC.

It is also proposed that electronic components, such as amplifying means, computing means, memory means, or driver electronics for the light emitting means, related to the gas cell, can be encapsulated in the EMC.

It is also proposed that optical components, such as optical filtering means, beam splitting means or optical gratings, related to the gas cell, are at least partly encapsulated in the EMC.

Gas filtering means, such as filter to prevent contamination of the cavity, can be positioned in the aperture, and such gas filtering means can be at least partly encapsulated in the EMC.

The inventive method teaches that the gas cell can be formed by means of transfer moulding. Even if traditional injection moulding in production can be made at much shorter cycle times, i.e. just a few seconds, whereas for transfer moulding the cycle times commonly are in the 1-2 minutes range, the CRE can still provide a low production cost for each part, since it is proposed to produce several gas cells in parallel in one and the same production tool, which will provide a production cost for each part that can be very economical.

It is proposed that a highly mineral filled Epoxy is used for the EMC.

Advantages

The advantages of a gas cell and a method according to the present invention is that the CRE technology packaging offers high production precision, excellent mechanical stability and good environmental protection, all the good properties requested by the industry, at a low manufacturing cost.

Advanced CRE makes it possible to allow certain areas of a component to be open and exposed to open air without getting covered by the moulding compound. If required it is also possible to cover such open areas with optically transparent EMC, which makes it possible to provide a partial or total encapsulation to protect the component from a dangerous environment.

BRIEF DESCRIPTION OF THE DRAWINGS

A gas cell and a method according to the present invention will now be described in detail with reference to the accompanying drawings, in which.

DESCRIPTION OF EMBODIMENTS AS PRESENTLY PREFERRED

Figure 1:
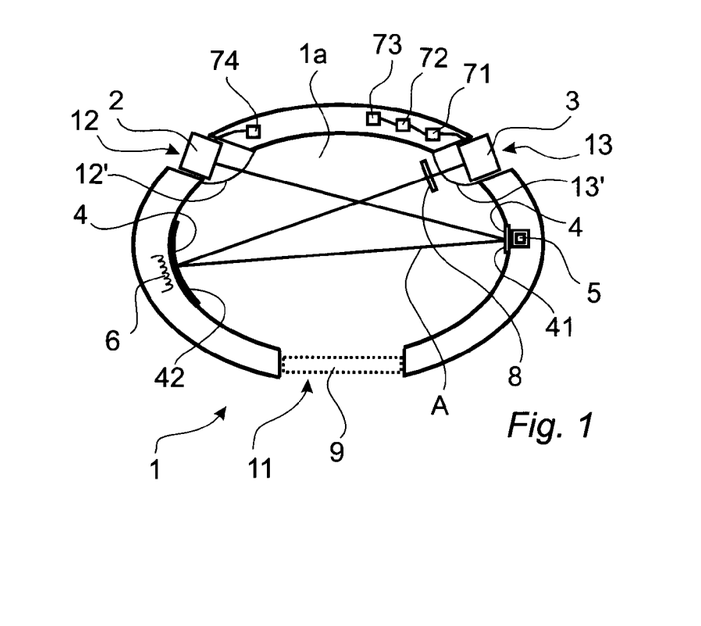
FIG. 1 is a schematic and very simplified cross sectional view of an inventive gas cell.

The present invention will now be described with reference to FIG. 1 showing a gas cell 1 for optical measurements of gas content and/or concentration. The gas cell comprises a cavity 1a, at least one aperture 11 for gas exchange, at least one first socket 12 for a light emitting means and at least one second socket 13 for a light detecting means. In the description of the present invention and in figures only one of each aperture 11, and first and second socket 12, 13 is shown for simplicity; however, it is obvious to the skilled person that several apertures and sockets can be used for different applications of a gas cell.

Several apertures can be used to enhance the gas exchange through the cavity, several first sockets can be used if several different light emitting means are used in order to use light emitting means with different wavelengths or to use different light emitting means for different optical paths through the gas cell, and several second sockets can be used if several light detecting means are used to detect light from different light emitting means with different wavelengths and/or to end the path of different optical paths through the gas cell. Optical components can be used to split the light from one light emitting means into several optical paths to be detected by several detecting means. It is also possible to have optical components through which several different optical paths from different light emitting means can be combined and detected by one detecting means.

Light emitting means 2 can be different kinds of light sources, such as sources with an incandescent filament providing a wide spectral range of wavelengths, or sources with a small range or single wavelengths, such as light emitting diodes or lasers. Light can be electromagnetic radiation of any wavelength depending on the specific implementation of the gas cell.

Light detecting means 3 can be any kind of sensor or detector adapted to detect either a specific wave length of received light or a wide range of wavelengths.

The length of an optical measuring path A through the cavity 1a is defined by a direct or indirect distance between a light emitting means in the first socket 12 and a light detecting means in the second socket 13. A direct path between the light emitting means 2 and the light receiving means 3 is a simple path but sometimes too short. The need of a long optical measuring path, in order to enhance the sensitivity of the gas cell, together with a demand of small sized gas cells required that the optical measuring path A is reflected one or several times through the cavity to get a sufficiently long measuring path with a small cavity. Thus the optical measuring path is often an indirect path between the light emitting means 2 and the light receiving means 3, where the path is reflected one or several times on reflecting means in the cavity 11. FIG. 1 shows an optical measuring path A that is reflected twice before reaching the light detecting means 3, hence it is defined by an indirect distance between the light emitting means and the light detecting means.

The present invention teaches that an epoxy mold compound (EMC) is used to form at least the part of the gas cell that defines the optical measuring path in the gas cell 1. When using EMC ceramic reinforced encapsulation (CRE) can be used to encapsulate different components in the gas cell 1 and thereby integrate and protect these components in the gas cell. This will also put the components in their intended positions with a very high accuracy and where their positions will be maintained even during wide temperature variations, humidity variations or mechanical stress of the gas cell, so that a well defined and stable optical measuring path A can be obtained between light emitting means 12 and light detecting means 13.

It is thus proposed that light emitting means 12 can be positioned in the first socket 2. This light emitting means 12 can be secured through some fastening means related to the first socket and/or it can be at least partly encapsulated in the EMC.

In order to provide protection of the light emitting means 2 it is proposed that the light emitting means 2 can be covered by optically transparent material 12', such as optically transparent EMC.

It is also proposed that light detecting means 3 can be positioned in the second socket 13, and that this light detecting means 3 is at least partly encapsulated in the EMC. Also the light detecting means 3 can be covered by optically transparent material 13'. This material can also be optically transparent EMC or it can be an optical filter with the further function of separating light wavelengths that are not to be detected from light wavelengths that are to be detected.

In order to provide a sufficiently long measuring path it is proposed that the cavity comprises at least one light reflecting means 4, where the measuring path A includes a reflection in the light reflecting means 4. This light reflecting means 4 can be a light reflecting mirror 41 which can be at least partly encapsulated in the EMC.

An example of a component that can be encapsulated in the EMC is a piezo transducer 5 that can be positioned behind the reflecting mirror 41, adapted to adjust the position of the reflecting mirror 41.

The light reflecting means 4 can also be a reflecting surface 42, and the shape of the reflecting surface 42 can be formed in the EMC.

Another example of a component that can be encapsulated in the EMC is heating means 6 that can be positioned behind the light reflecting means 4. Such heating means 6 can be any means adapted to provide heat to the reflecting means 4 in order to prevent fog to build up on the reflecting means 4 due to humidity in the gas within the gas cell 1. The figure shows that heating means 6 is positioned behind the reflective surface 42, it should be understood that it is also possible to position heating means behind the mirror 41 even if no such heating means are shown in the figure.

Other examples of components that can be encapsulated in the EMC are electronic components related to the gas cell, such as amplifying means 71, computing means 72, memory means 73, or driver electronics 74 for the light emitting means 2.

Yet other examples of components that can be at least partly encapsulated in the EMC are optical components related to the gas cell, such as optical filtering means 8, beam splitting means or optical gratings, beam splitting means and optical gratings not being illustrated in the figure.

It is also possible to have components such as gas filtering means 9 at least partly encapsulated in the EMC, where the gas filtering means 9 can be a filter to prevent contamination of the cavity 1, and which can be positioned in the aperture 11.

It is proposed that the EMC is a highly mineral filled Epoxy.

The present invention also relates to a method to form a gas cell 1 for optical measurements of gas content and/or concentration comprising a cavity 1a, at least one aperture 11 for gas exchange, at least one first socket 12 for a light emitting means and at least one second socket 13 for light detecting means, where the length of an optical measuring path A through the cavity 1a is defined by a direct or indirect distance between a light emitting means in the first socket 12 and a light detecting means in the second socket 13. The present invention specifically teaches that an epoxy mold compound (EMC) is used to form at least the part of the gas cell that defines the optical measuring path in the gas cell 1.

It is proposed that light emitting means 2 are positioned in the first socket 12, and that the light emitting means 2 is at least partly encapsulated in the EMC. It is also proposed that the light emitting means 2 can be covered by optically transparent material 12', such as optically transparent EMC.

In the same way, it is possible to position light detecting means 3 in the second socket 13, which light detecting means 3 can be at least partly encapsulated in the EMC.

Also the light detecting means 3 can be covered by optically transparent material 13', such as optically transparent EMC or an optical filter.

If the cavity 1a comprises at least one light reflecting means 4, where the measuring path includes a reflection in the light reflecting means 4, and if the light reflecting means 4 is a light reflecting mirror 41, it is proposed that the light reflecting mirror 41 is at least partly encapsulated in the EMC.

It is also possible to have a piezo transducer 5 positioned behind the reflecting mirror 41, adapted to adjust the position of the reflecting mirror 41, in which case it is proposed that the piezo transducer 5 can be encapsulated in the EMC.

If the cavity comprises at least one light reflecting means 4, where the measuring path includes a reflection in the light reflecting means 4, and if the light reflecting means 4 is a reflecting surface 42, it is proposed that the shape of the reflecting surface 42 is formed in the EMC.

Regardless of what kind of reflecting means 4 that are used, it is proposed that heating means 6 can be positioned behind the light reflecting means 4, and that the heating means 6 can be encapsulated in the EMC.

It is also proposed that electronic components related to the gas cell, such as amplifying means 71, computing means 72, memory means 73, or driver electronics 74 for the light emitting means 2, are encapsulated in the EMC.

It is also proposed that optical components related to the gas cell, such as optical filtering means 8, beam splitting means or optical gratings, can be at least partly encapsulated in the EMC.

It is also proposed that gas filtering means 9, such as a filter to prevent contamination of the cavity 1a, is positioned in the aperture 11, and that the gas filtering means 9 is at least partly encapsulated in the EMC.

Figure 2:
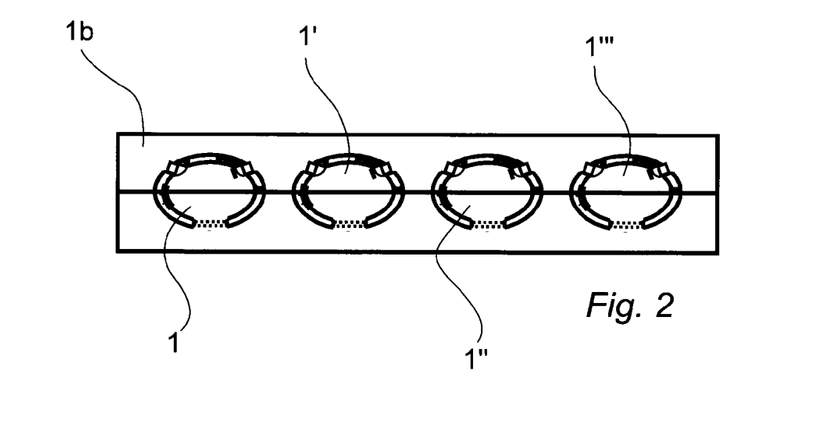
FIG. 2 is a schematic and very simplified illustration of a production tool through which several gas cells can be produced in parallel.

The present invention teaches that the gas cell 1 can be formed by means of transfer moulding, and FIG. 2 shows that several gas cells 1, 1', 1", 1''' can be produced in parallel in one and the same production tool 1b.

One proposed material to be used as EMC is a highly mineral filled Epoxy.

FIG. 1 is a very simplified and schematic illustration of the present invention were EMC is used to form the whole gas cell, however, the present invention relates to a gas cell where EMC is used to form at least the parts of the gas cell that define the optical measuring path.

Figure 3A:
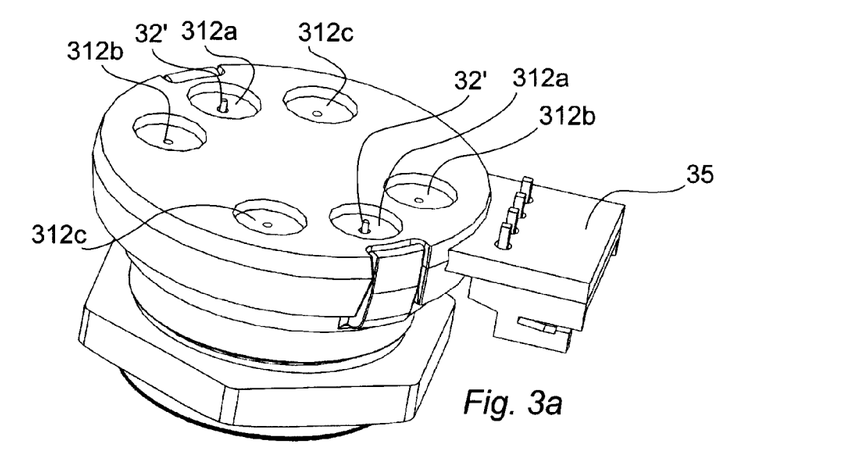
FIGS. 3a, 3b and 3c is a perspective and cross sectional view of first embodiment of a gas cell according to the present invention.
Figure 3B:
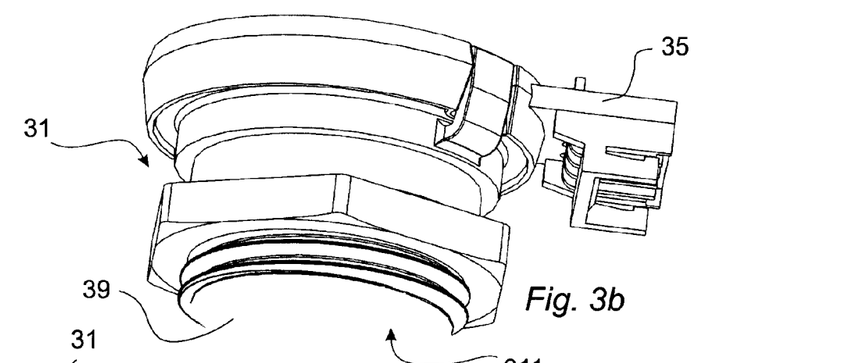
Figure 3C:
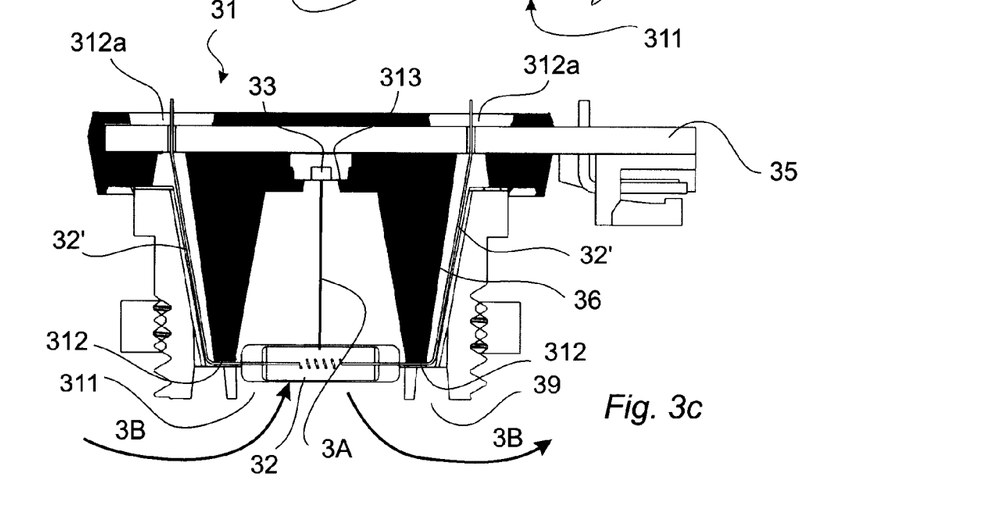

FIG. 3 is an example where EMC is used to form only one part of the gas cell 31. FIG. 3a shows a view of the gas cell 31 where three different pairs of openings 312a, 312b, 312c are shown, these openings being adapted to lead power connections 32' from the light emitting means 32 out of the gas cell for connection to a printed circuit board (PCB) 35 and other electronic components on the PCB.

FIGS. 3b and 3c shows that the aperture 311 of the gas cell 31 is covered by filtering means 39 adapted to allow a gas exchange 3B in and out of the gas cell while preventing contamination of the cavity 31a. FIG. 3c is a cross section of the gas cell, where the defining part 36 for the optical measuring path 3A is filled in with black. It can be seen that the light emitting means 32 is positioned in a first socket 312 and the light detecting means 33 is positioned in a second socket 313. The optical measuring path 3A goes straight from the light emitting means 32 to the light detecting means 33 and the distance is defined by the defining part 36. Since EMC is used to form at least the defining part 36 the optical measuring path is well defined and stable.

To show an example of dimensions in a macroscopic system it can be mentioned that the gas cell of FIG. 3 uses a lamp for a light source where the diameter of the lamp is 3 mm and the bolt that is screwed unto the outer part of the gas cell has an m16 thread.

Figure 4A:
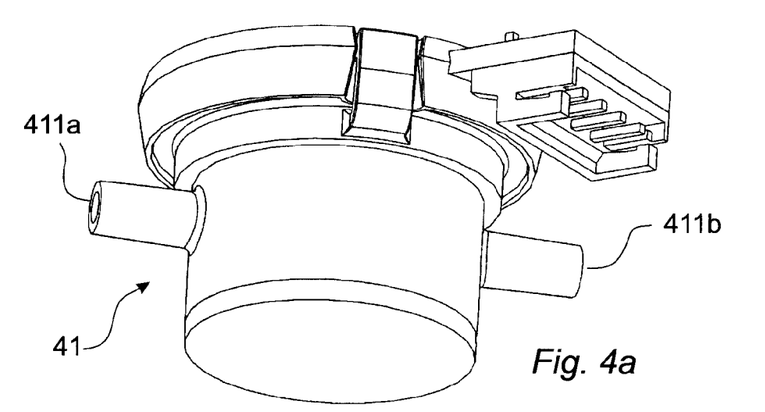
FIGS. 4a, 4b and 4c is a perspective and cross sectional view of second embodiment of a gas cell according to the present invention.
Figure 4B:
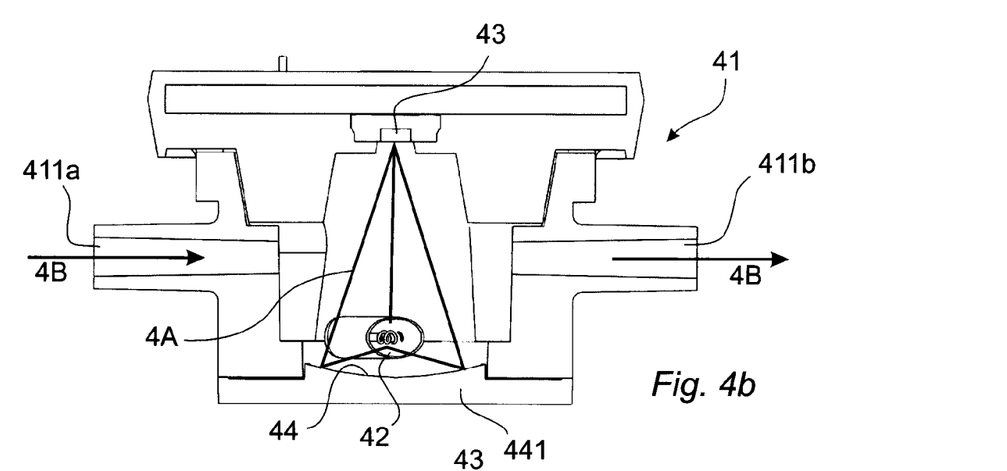
Figure 4C:
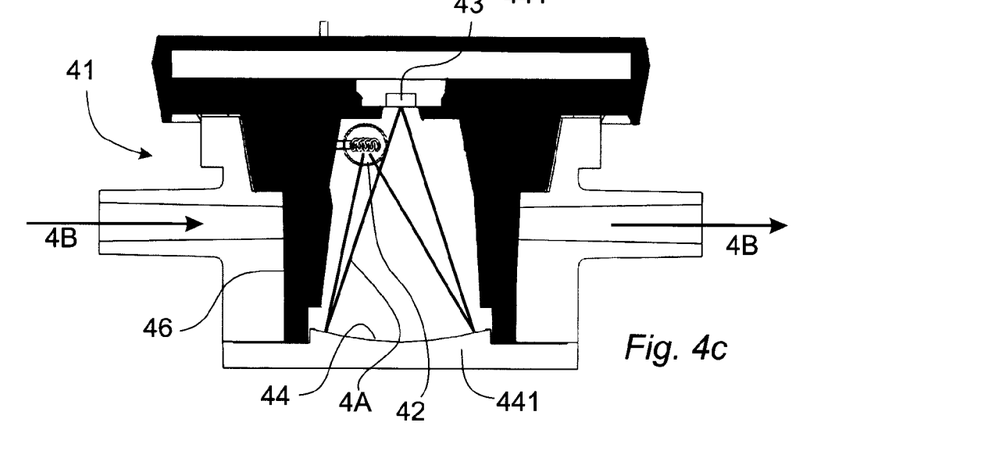

FIG. 4 shows a somewhat modified embodiment of a gas cell according to FIG. 3. Two apertures 411a, 411b are used to provide a gas exchange 4B in and out of the gas cell 41. These two apertures 411a, 411b are suited for a forced gas exchange where filtering means, if required, can be positioned anywhere in the forced gas flow.

A reflecting mirror 441 is positioned opposite to the light detecting means 43 acting as reflecting means 44.

In FIG. 4b an embodiment is shown where the light emitting means 42 is positioned in a first socket (not shown in the figure) placing the light emitting means 42 close to the reflecting mirror 441. The reflecting mirror has a concave shape reflecting and focusing the light emitted from the light emitting means towards the light detecting means 43.

FIG. 4c shows the same embodiment as in FIG. 4b, but where the light emitting means 42 has been positioned in a first socket (not shown in the figure) placing the light emitting means 42 close to the light detecting means 43. The optical measuring path 4A is indirect from the light emitting means 42, via the reflecting mirror 441, and to the light detecting means 43.

The defining part 46 provides a well defined and stable position for the light emitting means 42, the reflecting mirror 441 and the light detecting means 43, thus providing a well defined and stable optical measuring path 4A.

FIG. 5 shows another example of a gas cell 51 formed according to the present invention. FIG. 5a shows a cross sectional side view of the gas cell. Here it can be seen that a first defining part 561, shown in perspective view in FIG. 5b, comprises one first socket 512 with a light emitting device 52 and three second sockets 513a, 513b, 513c with three different detecting means 53a, 53b, 53c. A second defining part 562, shown in perspective in FIG. 5c, comprises a reflecting surface 54. EMC is used to form the first defining part 561 and the second defining part 562. The stable first defining part 561 will provide a precise and safe positioning and alignment of the emitting means 52 and the three detecting means 53a, 53b, 53c. The second defining part 562 will provide a reflecting surface 54 which is shaped in a form that will provide the intended reflection without distorting the wave front of the incoming light.

Figure 5A:
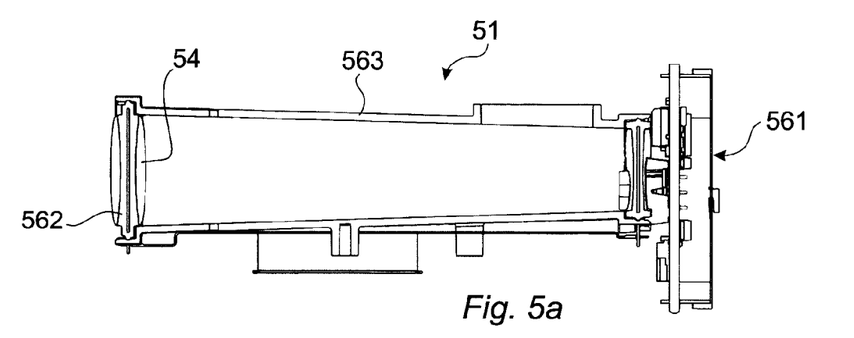
FIGS. 5a, 5b, 5c, 5d and 5e is a perspective and cross sectional view of a third embodiment of a gas cell according to the present invention.
Figure 5B:
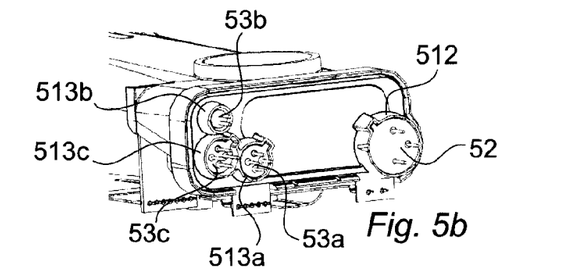
Figure 5C:
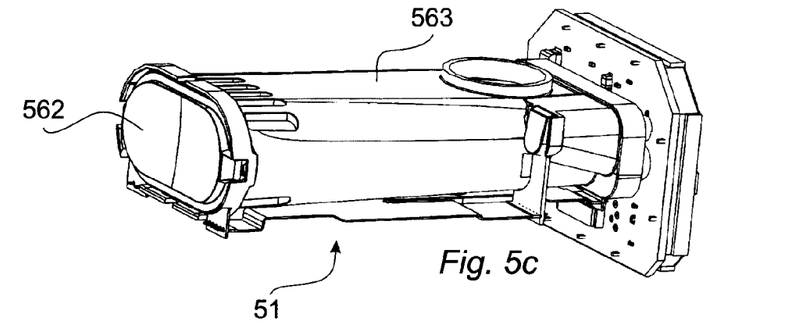
Figure 5D:
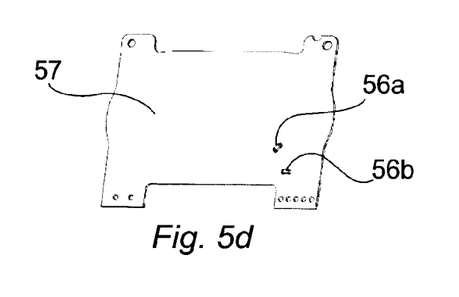

FIG. 5d shows a PCB 57 which is the molded into the second defining part 562. This PCB holds two heating means 56a, 56b adapted to heat the reflecting surface to avoid any condensation on the reflective surface 54.

Figure 5E:
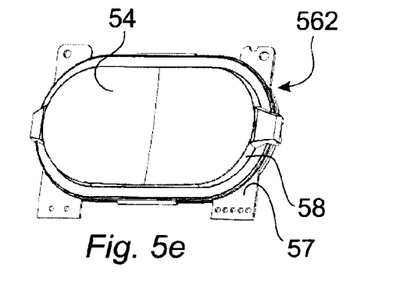

FIG. 5e shows the second defining part 562 where EMC 58 has been used to form the shape of the reflecting surface 54 and where the reflective surface has been metalized in order to provide the reflective properties. The two heating means 56a, 56b have been encapsulated in the EMC 58 that is forming the reflective surface 54.

When the first and second defining part 561, 562 are mounted to a tube shaped member 563 the gas cell 51 is formed and where EMC has been used to form the critical parts for the definition of the measuring path in the gas cell 51.

It may not be suitable to use EMC to form the tube shaped member 563 since this member can be relatively large or long in its elongated shape. If not possible through EMC then this member can be formed in any other way providing sufficient temperature stability.

To show another example of dimensions in a macroscopic system it can be mentioned that the gas cell of FIG. 5 is used in an alcohol meter where the distance between the light emitting device 52 and the reflecting surface 54 is in the order of 8 cm, and where the reflecting surface 54 has a surface of 2 cm×4 cm.

Parts that are not directly defining the optical measuring path can be produced in other ways; however, there is nothing that prevents that EMC is used to form also these parts.

It will be understood that the invention is not restricted to the aforedescribed and illustrated exemplifying embodiments thereof and that modifications can be made within the scope of the invention as defined by the accompanying Claims.

The invention claimed is:

1. A gas cell for optical measurements of gas content or concentration in a macroscopic system wherein a length of an optical measuring path is in the range of centimeters, the gas cell comprising:
  a cavity;
  at least one aperture for gas exchange;
  a plurality of sockets including a first socket for a light emitter and a second socket for a light detector; and
  an optical measuring path through the cavity, wherein a length of the optical measuring path is defined by a direct or indirect distance between the light emitter positioned in the first socket and the light detector positioned in the second socket, and wherein an epoxy mold compound is used to form at least the parts of the gas cell that form the length of the optical measuring path.

2. The gas cell according to claim 1, wherein the light emitter is positioned in the first socket, and wherein the light emitter is at least partly encapsulated in the epoxy mold compound.

3. The gas cell according to claim 2, wherein the light emitter is covered by optically transparent material.

4. The gas cell according to claim 3, wherein the optically transparent material is optically transparent epoxy mold compound.

5. The gas cell according to claim 1, wherein the light detector is positioned in the second socket, and wherein the light detector is at least partly encapsulated in the epoxy mold compound.

6. The gas cell according to claim 5, wherein the light detector is covered by optically transparent material.

7. The gas cell according to claim 6, wherein the optically transparent material is optically transparent epoxy mold compound.

8. The gas cell according to claim 6, wherein the optically transparent material is an optical filter.

9. The gas cell according to claim 1, further comprising at least one light reflector within the cavity, wherein the optical measuring path includes a reflection in the at least one light reflector.

10. The gas cell according to claim 9, wherein the light reflector is a light reflecting mirror, and wherein the light reflecting mirror is at least partly encapsulated in the epoxy mold compound.

11. The gas cell according to claim 10, further comprising a piezo transducer positioned behind the light reflecting mirror, wherein the piezo transducer is adapted to adjust the position of the light reflecting mirror, and wherein the piezo transducer is encapsulated in the epoxy mold compound.

12. The gas cell according to claim 9, wherein the light reflector is a reflecting surface formed in the epoxy mold compound.

13. The gas cell according to claim 9, further comprising a heating device, wherein the heating device is positioned behind the light reflector, and wherein the heating device is encapsulated in the epoxy mold compound.

14. The gas cell according to claim 1, further comprising electronic components, wherein the electronic components are chosen from the group comprising an amplifier, a computing device, a memory, or driver electronics for the light emitter, and wherein the electronic components are encapsulated in the epoxy mold compound.

15. The gas cell according to claim 1, further comprising optical components, wherein the optical components are chosen from the group comprising an optical filter, a beam splitter or an optical gratings, and wherein the optical components are at least partly encapsulated in the epoxy mold compound.

16. The gas cell according to claim 1, further comprising a gas filter to prevent contamination of the cavity, wherein the gas filter is positioned in the aperture, and wherein the gas filter is at least partly encapsulated in the epoxy mold compound.

17. The gas cell according to claim 1, wherein the epoxy mold compound is a highly mineral filled epoxy.

18. A method to form a gas cell for optical measurements of gas content or concentration in a macroscopic system where a length of an optical measuring path is in the range of centimeters, the gas cell comprising:
  a cavity;
  at least one aperture for gas exchange;
  a plurality of sockets including a first socket for a light emitter and a second socket for a light detector; and
  an optical measuring path through the cavity, wherein a length of the optical measuring path is defined by a direct or indirect distance between the light emitter positioned in the first socket and the light detector positioned in the second socket, and wherein an epoxy mold compound is used to form at least the part of the gas cell that forms a majority of the length of the optical measuring path.

19. The method according to claim 18, further comprising at least one light reflector within the cavity, wherein the optical measuring path includes a reflection in the light reflector, and wherein the light reflector is a light reflecting mirror, and wherein the light reflecting mirror is at least partly encapsulated in the epoxy mold compound.

20. The method according to claim 19, further comprising a piezo transducer positioned behind the light reflecting mirror, wherein the piezo transducer is adapted to adjust the position of the light reflecting mirror, and wherein the piezo transducer is encapsulated in the epoxy mold compound.

* * * * *